(12) United States Patent
Mygind et al.

(10) Patent No.: US 8,192,925 B2
(45) Date of Patent: Jun. 5, 2012

(54) POLYPEPTIDES HAVING ANTIMICROBIAL ACTIVITY AND POLYNUCLEOTIDES ENCODING SAME

(75) Inventors: Per Holse Mygind, Soeborg (DK); Mogens Trier Hansen, Lynge (DK); Marianne Vind Sorensen, Roskilde (DK); Dorthe Sandvang, Koebenhavn S. (DK)

(73) Assignee: Novozymes Adenium Biotech A/S, Bagsvaerd (DK)

( * ) Notice: Subject to any disclaimer, the term of this patent is extended or adjusted under 35 U.S.C. 154(b) by 789 days.

(21) Appl. No.: 12/119,626

(22) Filed: May 13, 2008

(65) Prior Publication Data

US 2012/0004159 A1     Jan. 5, 2012

Related U.S. Application Data

(62) Division of application No. 11/271,045, filed on Nov. 11, 2005, now Pat. No. 7,388,077.

(60) Provisional application No. 60/629,442, filed on Nov. 19, 2004.

(30) Foreign Application Priority Data

Nov. 12, 2004   (DK) ................................ 2004 01744

(51) Int. Cl.
   *C12Q 1/00*   (2006.01)
(52) U.S. Cl. .......................................................... 435/4
(58) Field of Classification Search .................... 435/4
   See application file for complete search history.

(56) References Cited

FOREIGN PATENT DOCUMENTS

| EP | 1146052 B1 | 3/1994 |
|---|---|---|
| FR | 2695392 A1 | 10/2001 |
| WO | 02/090384 A2 | 11/2002 |
| WO | WO 2004/108752 A1 | 12/2004 |
| WO | WO 2004/108757 A2 | 12/2004 |
| WO | WO 2006/014316 A1 | 2/2006 |

OTHER PUBLICATIONS

Bulet et al., Eur. J. Biochem, vol. 209, pp. 977-984 (1992).
Sambrook et al., Molecular Cloning, A Laboratory Manual, 3rd Edition, vol. 2, chapter 10, pp. 10.47-10.48 (2001).

*Primary Examiner* — Maryam Monshipouri
(74) *Attorney, Agent, or Firm* — Elias Lambiris

(57) ABSTRACT

The present invention relates to isolated polypeptides having antimicrobial activity and isolated polynucleotides encoding the polypeptides. The invention also relates to nucleic acid constructs, vectors, and host cells comprising the polynucleotides as well as methods for producing and using the polypeptides.

10 Claims, No Drawings

POLYPEPTIDES HAVING ANTIMICROBIAL ACTIVITY AND POLYNUCLEOTIDES ENCODING SAME

CROSS-REFERENCE TO RELATED APPLICATIONS

This application is a divisional of U.S. application Ser. No. 11/271,045 filed Nov. 11, 2005, now U.S. Pat. No. 7,388,077, which claims priority or the benefit under 35 U.S.C. 119 of Danish application no. PA 2004 01744 filed Nov. 12, 2004 and U.S. provisional application No. 60/629,442 filed Nov. 19, 2004, the contents of which are fully incorporated herein by reference.

FIELD OF THE INVENTION

The present invention relates to isolated polypeptides having antimicrobial activity and isolated polynucleotides encoding the polypeptides. The invention also relates to nucleic acid constructs, vectors, and host cells comprising the polynucleotides as well as methods for producing and using the polypeptides.

BACKGROUND OF THE INVENTION

It is an object of the present invention to provide polypeptides having antimicrobial activity and polynucleotides encoding the polypeptides.

SUMMARY OF THE INVENTION

The present invention relates to isolated polypeptides having antimicrobial activity selected from the group consisting of:
  (a) a polypeptide having an amino acid sequence which has at least 60% identity with amino acids 1 to 42 of SEQ ID NO:2;
  (b) a polypeptide which is encoded by a nucleotide sequence which hybridizes under at least medium stringency conditions with (i) nucleotides 145 to 270 of SEQ ID NO:1, (ii) the cDNA sequence contained in nucleotides 1 to 270 of SEQ ID NO:1, or (iii) a complementary strand of (i) or (ii); and
  (c) a variant comprising a conservative substitution, deletion, and/or insertion of one or more amino acids of amino acids 1 to 42 of SEQ ID NO:2.

The present invention also relates to isolated polynucleotides encoding polypeptides having antimicrobial activity, selected from the group consisting of:
  (a) a polynucleotide encoding a polypeptide having an amino acid sequence which has at least 60% identity with amino acids 1 to 42 of SEQ ID NO:2;
  (b) a polynucleotide having at least 60% identity with nucleotides 145 to 270 of SEQ ID NO:1, and
  (c) a polynucleotide which hybridizes under at least medium stringency conditions with (i) nucleotides 145 to 270 of SEQ ID NO:1, (ii) the cDNA sequence contained in nucleotides 1 to 270 of SEQ ID NO:1, or (iii) a complementary strand of (i) or (ii).

The present invention also relates to nucleic acid constructs, recombinant expression vectors, and recombinant host cells comprising the polynucleotides.

The present invention also relates to methods for producing such polypeptides having antimicrobial activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides and polynucleotides of the invention.

DEFINITIONS

Antimicrobial activity: The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect, wherein the term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

For purposes of the present invention, antimicrobial activity may be determined according to the procedure described by Lehrer et al., Journal of Immunological Methods, Vol. 137 (2) pp. 167-174 (1991). Alternatively, antimicrobial activity may be determined according to the NCCLS guidelines from CLSI (Clinical and Laboratory Standards Institute; formerly known as National Committee for Clinical and Laboratory Standards).

Polypeptides having antimicrobial activity may be capable of reducing the number of living cells of *Escherichia coli* (DSM 1576) to ¹⁄₁₀₀ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

Polypeptides having antimicrobial activity may be capable of reducing the number of living cells of *Bacillus subtilis* (ATCC 6633) to ¹⁄₁₀₀ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the antimicrobial activity of the polypeptide consisting of the amino acid sequence shown as amino acids 1 to 42 of SEQ ID NO:2.

Defensin: The term "defensin" as used herein refers to polypeptides recognized by a person skilled in the art as belonging to the defensin class of antimicrobial peptides. To determine if a polypeptide is a defensin according to the invention, the amino acid sequence is preferably compared with the hidden markov model profiles (HMM profiles) of the PFAM database by using the freely available HMMER software package (see Example 6).

The PFAM defensin families include Defensin_1 or "Mammalian defensin" (accession no. PF00323), Defensin_2 or "Arthropod defensin" (accession no. PF01097), Defensin_beta or "Beta Defensin" (accession no. PF00711), Defensin_propep or "Defensin propeptide" (accession no. PF00879) and Gamma-thionin or "Gamma-thionins family" (accession no. PF00304).

The defensins may belong to the alpha-defensin class, the beta-defensin class, the theta-defensin class, the insect (arthropod) defensin class, the plant defensin class, the mussel defensin class, or other defensin classes wherein the amino acid sequence comprises 6 or 8 cysteines and are structurally similar to any of the before-mentioned defensin classes. The defensins may also be synthetic defensins sharing the characteristic features of any of the defensin classes.

Examples of such defensins include, but are not limited to, α-Defensin HNP-1 (human neutrophil peptide) HNP-2 and HNP-3; β-Defensin-12, Drosomycin, Heliomicin, γ1-purothionin, Insect defensin A, and the defensins disclosed in PCT applications WO 99/53053, WO 02/085934 and WO 03/044049.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences may be determined by using the program FASTA included in version 2.0x of the FASTA program package (see W. R. Pearson and D. J. Lipman (1988), "Improved Tools for Biological Sequence Analysis", PNAS 85:2444-2448; and W. R. Pearson (1990) "Rapid and Sensitive Sequence Comparison with FASTP and FASTA", Methods in Enzymology 183:63-98). The scoring matrix used was BLOSUM50, gap penalty was −12, and gap extension penalty was −2.

The degree of identity between two nucleotide sequences is determined using the same algorithm and software package as described above. The scoring matrix used was the identity matrix, gap penalty was −16, and gap extension penalty was −4.

Alternatively, an alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1 to 42 of SEQ ID NO:2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence (e.g. the length of amino acids 1 to 42 of SEQ ID NO:2 is 42).

In the alignment example below, the overlap is the amino acid sequence "HTWGER-NL" of Sequence 1; or the amino acid sequence "HGWGEDANL" of Sequence 2. In the example a gap is indicated by a "-".

Alignment Example

```
Sequence 1: ACMSHTWGER-NL
              | ||| ||
Sequence 2:    HGWGEDANLAMNPS
```

Polypeptide Fragment: The term "polypeptide fragment" is defined herein as a polypeptide having one or more amino acids deleted from the amino and/or carboxyl terminus of SEQ ID NO:2 or a homologous sequence thereof, wherein the fragment has antimicrobial activity. Preferably a polypeptide fragment of the invention retains all cysteine residues and the amino acid residues between the cysteine residues.

Subsequence: The term "subsequence" is defined herein as a nucleotide sequence having one or more nucleotides deleted from the 5' and/or 3' end of SEQ ID NO:1 or a homologous sequence thereof, wherein the subsequence encodes a polypeptide fragment having antimicrobial activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the amino acids 1 to 42 of SEQ ID NO:2 as well as genetic manipulation of the DNA encoding that polypeptide. The modification(s) can be substitution(s), deletion(s) and/or insertions(s) of the amino acid(s) as well as replacement(s) of amino acid side chain(s); or use of unnatural amino acids with similar characteristics in the amino acid sequence. In particular the modification(s) can be amidations, such as amidation of the C-terminus.

Artificial variant: When used herein, the term "artificial variant" means a polypeptide having antimicrobial activity produced by an organism expressing a modified nucleotide sequence of SEQ ID NO:1. The modified nucleotide sequence is obtained through human intervention by modification of the nucleotide sequence disclosed in SEQ ID NO:1.

DETAILED DESCRIPTION OF THE INVENTION

Polypeptides Having Antimicrobial Activity

In a first aspect, the present invention relates to isolated polypeptides having an amino acid sequence which has a degree of identity to amino acids 1 to 42 of SEQ ID NO:2 (i.e., the mature polypeptide) of at least 60%, preferably at least 65%, more preferably at least 70%, more preferably at least 75%, more preferably at least 80%, more preferably at least 85%, even more preferably at least 90%, most preferably at least 95%, and even most preferably at least 97%, which have antimicrobial activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 1 to 42 of SEQ ID NO:2.

A polypeptide of the present invention preferably comprises the amino acid sequence of SEQ ID NO:2 or an allelic variant thereof; or a fragment thereof that has antimicrobial activity. In a preferred aspect, a polypeptide comprises the amino acid sequence of SEQ ID NO:2. In another preferred aspect, a polypeptide comprises amino acids 1 to 42 of SEQ ID NO:2, or an allelic variant thereof; or a fragment thereof that has antimicrobial activity. In another preferred aspect, a polypeptide comprises amino acids 1 to 42 of SEQ ID NO:2. In another preferred aspect, a polypeptide consists of the amino acid sequence of SEQ ID NO:2 or an allelic variant thereof; or a fragment thereof that has antimicrobial activity. In another preferred aspect, a polypeptide consists of the amino acid sequence of SEQ ID NO:2. In another preferred aspect, a polypeptide consists of amino acids 1 to 42 of SEQ ID NO:2 or an allelic variant thereof; or a fragment thereof that has antimicrobial activity. In another preferred aspect, a polypeptide consists of amino acids 1 to 42 of SEQ ID NO:2.

In a second aspect, the present invention relates to isolated polypeptides having antimicrobial activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 145 to 270 of SEQ ID NO:1, (ii) the cDNA sequence contained in nucleotides 1 to 270 of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). A subsequence of SEQ ID NO:1 contains at least 100 contiguous nucleotides or preferably at least 200 contiguous nucleotides. Moreover, the subsequence may encode a polypeptide fragment which has antimicrobial activity.

The nucleotide sequence of SEQ ID NO:1 or a subsequence thereof, as well as the amino acid sequence of SEQ ID NO:2 or a fragment thereof, may be used to design a nucleic acid probe to identify and clone DNA encoding polypeptides having antimicrobial activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 270 nucleotides. Both DNA and RNA probes can be used. The probes are typically labeled for detecting the corresponding gene (for example, with $^{32}P$, $^3H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having antimicrobial activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO:1, its complementary strand, or a subsequence thereof, under very low to very high stringency conditions. Molecules to which the nucleic acid probe hybridizes under these conditions can be detected using X-ray film.

In a preferred aspect, the nucleic acid probe is a polynucleotide sequence which encodes the polypeptide of SEQ ID NO:2, or a subsequence thereof. In another preferred aspect, the nucleic acid probe is SEQ ID NO:1. In another preferred aspect, the nucleic acid probe is the mature polypeptide coding region of SEQ ID NO:1.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to artificial variants comprising a conservative substitution, deletion, and/or insertion of one or more amino acids of SEQ ID NO:2 or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., antimicrobial activity) to identify amino acid residues that are critical to the activity of the molecule. See also, Hilton of al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman of al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino adds 1 to 42 of SEQ ID NO:2 is 10, preferably 9, more preferably 8, more preferably 7, more preferably at most 6, more preferably at most 5, more preferably 4, even more preferably 3, most preferably 2, and even most preferably 1.

In a preferred embodiment, the polypeptides of the invention are defensin polypeptides. In another embodiment, the polypeptides of the invention comprise three di-cysteine bonds.

N-Terminal Extension

An N-terminal extension of the polypeptides of the invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

Kex2 Sites

Kex2 sites (see, e.g., Methods in Enzymology Vol 185, ed. D. Goeddel, Academic Press Inc. (1990), San Diego, Calif., "Gene Expression Technology") and kex2-like sites are di-basic recognition sites (i.e., cleavage sites) found between the pro-peptide encoding region and the mature region of some proteins.

Insertion of a kex2 site or a kex2-like site have in certain cases been shown to improve correct endopeptidase processing at the pro-peptide cleavage site resulting in increased protein secretion levels.

In the context of the invention insertion of a kex2 or kex2-like site result in the possibility to obtain cleavage at a certain position in the N-terminal extension resulting in an antimicrobial polypeptide being extended in comparison to the mature polypeptide shown as amino acids 1 to 42 of SEQ ID NO:2.

Fused Polypeptides

The polypeptides of the present invention also include fused polypeptides or cleavable fusion polypeptides in which another polypeptide is fused at the N-terminus or the C-terminus of the polypeptide of the invention or a fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Sources of Polypeptides Having Antimicrobial Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having antimicrobial activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

In another preferred aspect, the polypeptide is a *Eurotium amstelodami, Aspergillus amstelodami, Aspergillus montevidensis* or *Aspergillus vitis* polypeptide.

In a more preferred aspect, the polypeptide is a *Eurotium amstelodami* polypeptide, e.g., the polypeptide of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. In a preferred aspect, the nucleotide sequence is set forth in SEQ ID NO:1. In another preferred aspect, the nucleotide sequence is the mature polypeptide coding region of SEQ ID NO:1. The present invention also encompasses nucleotide sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode fragments of SEQ ID NO:2 that have antimicrobial activity.

The present invention also relates to mutant polynucleotides comprising at least one mutation in the mature polypeptide coding sequence of SEQ ID NO:1, in which the mutant nucleotide sequence encodes a polypeptide which consists of amino acids 1 to 42 of SEQ ID NO:2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Eurotium*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO:1 (i.e., nucleotides 145 to 270) of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO:1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for antimicrobial activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under low stringency conditions, preferably medium stringency conditions, more preferably medium-high stringency conditions, even more preferably high stringency conditions, and most preferably very high stringency conditions with (i) nucleotides 145 to 270 of SEQ ID NO:1, (ii) the cDNA sequence contained in nucleotides 1 to 270 of SEQ ID NO:1, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under low, medium, medium-high, high, or very high stringency conditions with (i) nucleotides 145 to 270 of SEQ ID NO:1, (ii) the cDNA sequence contained in nucleotides 1 to 270 of SEQ ID NO:1, or (iii) a complementary strand of (i) or (ii); and (b) isolating the hybridizing polynucleotide, which encodes a polypeptide having antimicrobial activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* those phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3- phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred aspect, the signal peptide coding region is nucleotides 1 to 60 of SEQ ID NO:1 which encode amino acids −48 to −29 of SEQ ID NO:2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (npr7), *Saccharomyces cerevisiae* alpha-factor, *Rhizomucor miehei* aspartic proteinase, and *Myceliophthora thermophila* laccase (WO 95/33836).

In a preferred aspect, the propeptide coding region is nucleotides 61 to 144 of SEQ ID NO:1 which encode amino acids −28 to −1 of SEQ ID NO:2.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the daI genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacterial, Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium suiphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, Journal of Bacteriology 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Eurotium*, and more preferably *Eurotium amstelodami*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO:1, wherein the mutant nucleotide sequence encodes a polypeptide which consists of amino acids 1 to 42 of SEQ ID NO:2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies. For example, an antimicrobial activity assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having antimicrobial activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV, the maize ubiquitin 1, and the rice actin 1 promoter may be used (Franck et al., 1980, *Cell* 21: 285-294, Christensen at al., 1992, *Plant Mo. Biol.* 18: 675-689; Zhang at al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mot Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mita and Higgins, 1994, *Plant Molecular Biology* 26: 85-93), or the aldP gene promoter from rice (Kagaya at al., 1995, *Molecular and General Genetics* 248: 668-674), or a wound inducible promoter such as the potato pint promoter (Xu at, 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having antimicrobial activity of the present invention under conditions conducive for production of the polypeptide; and (b) recovering the polypeptide.

Compositions

The present invention also relates to compositions, such as pharmaceutical compositions, comprising a polypeptide of the present invention. Preferably, the compositions are enriched in such a polypeptide. The term "enriched" indicates that the antimicrobial activity of the composition has been increased, e.g., with an enrichment factor of 1.1.

The compositions may further comprise another pharmaceutically active agent, such as an additional biocidal agent, such as another antimicrobial polypeptide exhibiting antimicrobial activity as defined above. The biocidal agent may be an antibiotic, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. The biocidal agent may also be an anti-mycotic agent, including polyenes, e.g. amphotericin B, nystatin; 5-flucosyn; and azoles, e.g. miconazol, ketoconazol, itraconazol and fluconazol.

In an embodiment the biocidal agent is a non-enzymatic chemical agent. In another embodiment the biocidal agent is a non-polypeptide chemical agent.

The compositions may comprise a suitable carrier material. The compositions may also comprise a suitable delivery vehicle capable of delivering the antimicrobial polypeptides of the invention to the desired locus when the compositions are used as a medicament.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Methods and Uses

The present invention is also directed to methods for using the polypeptides having antimicrobial activity. The antimicrobial polypeptides are typically useful at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, the present invention may also be used in all applications for which known antimicrobial compositions are useful, such as protection of wood, latex, adhesive, glue, paper, cardboard, textile, leather, plastics, caulking, and feed.

Other uses include preservation of foods, beverages, cosmetics such as lotions, creams, gels, ointments, soaps, shampoos, conditioners, antiperspirants, deodorants, mouth wash, contact lens products, or food ingredients.

Thus, the antimicrobial polypeptides of the invention may by useful as a disinfectant, e.g., in the treatment of infections in the eye or the mouth, skin infections; in antiperspirants or deodorants; for cleaning and disinfection of contact lenses and teeth (oral care).

In general it is contemplated that the antimicrobial polypeptides of the present invention are useful for cleaning, disinfecting or inhibiting microbial growth on any surface. Examples of surfaces, which may advantageously be contacted with the antimicrobial polypeptides of the invention are surfaces of process equipment used e.g. dairies, chemical or pharmaceutical process plants, water sanitation systems, oil processing plants, paper pulp processing plants, water treatment plants, and cooling towers. The antimicrobial polypeptides of the invention should be used in an amount, which is effective for cleaning, disinfecting or inhibiting microbial growth on the surface in question.

The antimicrobial polypeptides of the invention may additionally be used for cleaning surfaces and cooking utensils in food processing plants and in any area in which food is prepared or served such as hospitals, nursing homes, and restaurants.

It may also be used as a preservation agent or a disinfection agent in water based paints.

The invention also relates to the use of an antimicrobial polypeptide or composition of the invention as a medicament. Further, an antimicrobial polypeptide or composition of the invention may also be used for the manufacture of a medicament for controlling or combating microorganisms, such as fungal organisms or bacteria, preferably gram positive bacteria.

The composition and antimicrobial polypeptide of the invention may be used as an antimicrobial veterinarian or human therapeutic or prophylactic agent. Thus, the composition and antimicrobial polypeptide of the invention may be used in the preparation of veterinarian or human therapeutic agents or prophylactic agents for the treatment of microbial infections, such as bacterial or fungal infections, preferably gram positive bacterial infections. In particular the microbial infections may be associated with lung diseases including, but not limited to, tuberculosis, pneumonia and cystic fibrosis; and sexual transmitted diseases including, but not limited to, gonorrhea and chlamydia.

The composition of the invention comprises an effective amount of the antimicrobial polypeptide of the invention.

The term "effective amount" when used herein is intended to mean an amount of the antimicrobial polypeptides of the invention, which is sufficient to inhibit growth of the microorganisms in question.

The invention also relates to wound healing compositions or products such as bandages, medical devices such as, e.g., catheters and further to anti-dandruff hair products, such as shampoos.

Formulations of the antimicrobial polypeptides of the invention are administered to a host suffering from or predisposed to a microbial infection. Administration may be topical, localized or systemic, depending on the specific microorganism, preferably it will be localized. Generally the dose of the antimicrobial polypeptides of the invention will be sufficient to decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use. The antimicrobial polypeptides of the invention are particularly useful for killing gram negative bacteria, including *Pseudomonas aeruginosa*, and *Chlamydia trachomatis*; and gram-positive bacteria, including streptococci such as *Streptococcus pneumonia*, *S. uberis, S. hyointestinalis, S. pyogenes* or *agalactiae*; and staphylococci such as *Staphylococcus aureus, S. epidermidis, S. simulans, S. xylosus, S. camosus*.

Formulations of the antimicrobial polypeptides of the invention may be administered to a host suffering from or predisposed to a microbial lung infection, such as pneumonia; or to a microbial wound infection, such as a bacterial wound infection.

Formulations of the antimicrobial polypeptides of the invention may also be administered to a host suffering from or predisposed to a skin infection, such as acne, atopic dermatitis or seborrheic dermatitis; preferably the skin infection is a bacterial skin infection, e.g. caused by *Staphylococcus epidermidis, Staphylococcus aureus, Propionibacterium acnes, Pityrosporum ovale* or *Malassezia furfur*.

The antimicrobial polypeptides of the invention are also useful for in vitro formulations to kill microbes, particularly where one does not wish to introduce quantities of conventional antibiotics. For example, the antimicrobial polypeptides of the invention may be added to animal and/or human food preparations; or they may be included as an additive for in vitro cultures of cells, to prevent the overgrowth of microbes in tissue culture.

The susceptibility of a particular microbe to killing with the antimicrobial polypeptides of the invention may be determined by in vitro testing, as detailed in the experimental section. Typically a culture of the microbe is combined with the antimicrobial polypeptide at varying concentrations for a period of time sufficient to allow the protein to act, usually between about one hour and one day. The viable microbes are then counted, and the level of killing determined.

Microbes of interest include, but are not limited to, Gram-negative bacteria, for example: *Citrobacter* sp.; *Enterobacter* sp.; *Escherichia* sp., e.g. *E. coli*; *Klebsiella* sp.; *Morganella* sp.; *Proteus* sp.; *Providencia* sp.; *Salmonella* sp., e.g. *S. typhi, S. typhimurium*; *Serratia* sp.; *Shigella* sp.; *Pseudomonas* sp., e.g. *P. aeruginosa*; *Yersinia* sp., e.g. *Y. pestis, Y. pseudotuberculosis, Y. enterocolitica*; *Franciscella* sp.; *Pasturella* sp.; *Vibrio* sp., e.g. *V. cholerae, V. parahemolyticus*; *Campylobacter* sp., e.g. *C. jejuni*; *Haemophilus* sp., e.g. *H. influenzae, H. ducreyi*; *Bordetella* sp., e.g. *B. pertussis, B. bronchiseptica, B. parapertussis*; *Brucella* sp., *Neisseria* sp., e.g. *N. gonorrhoeae, N. meningitidis*, etc. Other bacteria of interest include *Legionella* sp., e.g. *L. pneumophila*; *Listeria* sp., e.g. *L. monocytogenes*; *Mycoplasma* sp., e.g. *M. hominis, M. pneumoniae*; *Mycobacterium* sp., e.g. *M. tuberculosis, M. leprae*; *Treponema* sp., e.g. *T. pallidum*; *Borrelia* sp., e.g. *B. burgdorferi*; *Leptospirae* sp.; *Rickettsia* sp., e.g. *R. rickettsii, R. typhi*; *Chlamydia* sp., e.g. *C. trachomatis, C. pneumoniae, C. psittaci*; *Helicobacter* sp., e.g. *H. pylori*, etc.

Non-bacterial pathogens of interest include fungal and protozoan pathogens, e.g. *Plasmodia* sp., e.g. *P. falciparum, Trypanosoma* sp., e.g. *T. brucei*; shistosomes; *Entaemoeba* sp., *Cryptococcus* sp., *Candida* sp., e.g. *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific antimicrobial polypeptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The antimicrobial polypeptides of the invention may be systemic after administration or may be localized by the use of an implant or other formulation that acts to retain the active dose at the site of implantation.

In one embodiment, a formulation for topical use comprises a chelating agent that decreases the effective concentration of divalent cations, particularly calcium and magnesium. For example, agents such as citrate, EGTA or EDTA may be included, where citrate is preferred. The concentration of citrate will usually be from about 1 to 10 mM.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al., (1991) *J. Biol. Chem.* 266:3361 may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with Other Active Agents

For use in the subject methods, the antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g. interferon gamma, tumor necrosis factor alpha, interleukin 12, etc.

In Vitro Synthesis

The antimicrobial peptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein Animal Feed The present invention is also directed to methods for using the polypeptides having antimicrobial activity in animal feed, as well as to feed compositions and feed additives comprising the antimicrobial polypeptides of the invention.

The term animal includes all animals, including human beings. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal.

In the use according to the invention the antimicrobial polypeptide can be fed to the animal before, after, or simultaneously with the diet. The latter is preferred.

In a particular embodiment, the antimicrobial polypeptide, in the form in which it is added to the feed, or when being included in a feed additive, is well defined. Well-defined means that the antimicrobial polypeptide preparation is at least 50% pure as determined by Size-exclusion chromatography (see Example 12 of WO 01/58275). In other particular embodiments the antimicrobial polypeptide preparation is at least 60, 70, 80, 85, 88, 90, 92, 94, or at least 95% pure as determined by this method.

A well-defined antimicrobial polypeptide preparation is advantageous. For instance, it is much easier to dose correctly to the feed an antimicrobial polypeptide that is essentially free from interfering or contaminating other antimicrobial polypeptides. The term dose correctly refers in particular to the objective of obtaining consistent and constant results, and the capability of optimising dosage based upon the desired effect.

For the use in animal feed, however, the antimicrobial polypeptide need not be that pure; it may e.g. include other enzymes, in which case it could be termed an antimicrobial polypeptide preparation.

The antimicrobial polypeptide preparation can be (a) added directly to the feed (or used directly in a treatment process of vegetable proteins), or (b) it can be used in the production of one or more intermediate compositions such as feed additives or premixes that is subsequently added to the feed (or used in a treatment process). The degree of purity described above refers to the purity of the original antimicrobial polypeptide preparation, whether used according to (a) or (b) above.

Antimicrobial polypeptide preparations with purities of this order of magnitude are in particular obtainable using recombinant methods of production, whereas they are not so easily obtained and also subject to a much higher batch-to-batch variation when the antimicrobial polypeptide is produced by traditional fermentation methods.

Such antimicrobial polypeptide preparation may of course be mixed with other enzymes.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The antimicrobial polypeptide can be added to the feed in any form, be it as a relatively pure antimicrobial polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the antimicrobial polypeptide of the invention, the animal feed additives of the invention contain at least one fat soluble vitamin, and/or at least one water soluble vitamin, and/or at least one trace mineral, and/or at least one macro mineral.

Further, optional, feed-additive ingredients are colouring agents, aroma compounds, stabilisers, and/or at least one other enzyme selected from amongst phytases EC 3.1.3.8 or 3.1.3.26; xylanases EC 3.2.1.8; galactanases EC 3_2.1.89; and/or beta-glucanases EC 3.2.1.4.

In a particular embodiment these other enzymes are well defined (as defined above for antimicrobial polypeptide preparations).

Examples of other antimicrobial peptides (AMP's) are CAP18, Leucocin A, Tritrpticin, Protegrin-1, Thanatin, Defensin, Ovispirin such as Novispirin (Robert Lehrer, 2000), and variants, or fragments thereof which retain antimicrobial activity.

Examples of other antifungal polypeptides (AFP's) are the *Aspergillus* giganteus, and *Aspergillus niger* peptides, as well as variants and fragments thereof which retain antifungal activity, as disclosed in WO 94/01459 and WO 02/090384.

Usually fat and water soluble vitamins, as well as trace minerals form part of a so-called premix intended for addition to the feed, whereas macro minerals are usually separately added to the feed. Either of these composition types, when enriched with an antimicrobial polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat soluble vitamins are vitamin A, vitamin D3, vitamin E, and vitamin K, e.g. vitamin K3.

Examples of water soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one antimicrobial polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey. Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 5-30 mg enzyme protein per kg animal diet.

The antimicrobial polypeptide may be administered in one or more of the following amounts (dosage ranges): 0.01-200; or 0.01-100; or 0.05-100; or 0.05-50; or 0.10-10—all these ranges being in mg antimicrobial polypeptide protein per kg feed (ppm).

For determining mg antimicrobial polypeptide protein per kg feed, the antimicrobial polypeptide is purified from the feed composition, and the specific activity of the purified antimicrobial polypeptide is determined using a relevant assay (see under antimicrobial activity, substrates, and assays). The antimicrobial activity of the feed composition as such is also determined using the same assay, and on the basis of these two determinations, the dosage in mg antimicrobial polypeptide protein per kg feed is calculated.

The same principles apply for determining mg antimicrobial polypeptide protein in feed additives. Of course, if a sample is available of the antimicrobial polypeptide used for preparing the feed additive or the feed, the specific activity is determined from this sample (no need to purify the antimicrobial polypeptide from the feed composition or the additive).

Signal Peptide and Propeptide

The present invention also relates to nucleic acid constructs comprising a gene encoding a protein operably linked to one or both of a first nucleotide sequence consisting of nucleotides 1 to 60 of SEQ ID NO:1 encoding a signal peptide consisting of amino acids −48 to −29 of SEQ ID NO:2 and a second nucleotide sequence consisting of nucleotides 61 to 144 of SEQ ID NO:1 encoding a propeptide consisting of amino acids −28 to −1 of SEQ ID NO:2, wherein the gene is foreign to the first and second nucleotide sequences.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The first and second nucleotide sequences may be operably linked to foreign genes individually with other control sequences or in combination with other control sequences. Such other control sequences are described supra. As described earlier, where both signal peptide and propeptide regions are present at the amino terminus of a protein, the propeptide region is positioned next to the amino terminus of a protein and the signal peptide region is positioned next to the amino terminus of the propeptide region.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade. In the following examples, the antimicrobial polypeptide shown as amino acids 1 to 42 of SEQ ID NO:2 is referred to as "Eurocin".

Example 1 cDNA library of *Eurotium amstelodami*

A cDNA library was prepared from *E. amstelodami* grown for 5 days on Potato dextrose agar (PDA). PolyA enriched RNA was purified, cDNA was synthesized and the library made according to standard molecular biology procedures. A detailed protocol on the general process can be found in the examples of international patent application WO 01/12794. The vector used for cloning was pMhas5, which is shown in SEQ ID NO:8, and which has the following features:

TABLE 1

Features of vector pMhas5.

| Feature | Location | Description |
|---|---|---|
| CDS | 365-1156 | Kanamycin resistance |
| CDS | 2232-2387 | Beta galactosidase alpha peptide |
| −10 signal | 2189-2192 | Shine Dalgarno |
| promotor | 2101-2189 | Lac promotor |
| misc feature | 626-650 | KanP1 primer for BACE system |

Example 2

Construction of an *Aspergillus* Expression Vector for Eurocin

The Eurocin encoding nucleotide sequence was amplified from the cDNA library (see Example 1) in the following manner: 1 microliter of cDNA (approximately 10 nanogram of DNA) was used as template in a PCR reaction with Primer A and Primer B.

```
                                             (SEQ ID NO: 4)
Primer A: TCTTGGATCCACCATGCACTTCACCAAGGTCTCC (SEQ ID NO: 5)
Primer B: TCTTCTCGAGTTAGAAAGAACAGGTGCAGGTAGG
```

10 pmole of each primer was used in a 50 microliter reaction volume. Annealing temperature was 55 degrees Celsius and extension at 72 degrees Celsius for 1 minute. A total of 35 cycles were run. The Expand High Fidelity PCR System (Roche) was used.

Aliquots of the PCR reaction were separated on a 4% agarose gel. A distinct band was seen at a size of approximately 300 bp. The PCR fragment was digested with BamH1 and Xho1 which cut in the overhangs introduced by the PCR primers. The digested fragments were isolated and cloned into BamH1-Xho1 digested pMT2786, an *Aspergillus* expression plasmid based on the plasmid pMT2188, which is based on pCaHj527 (se Example 7 of international patent application WO 02/12472; and WO 00/70064). The sequence of the insert was verified to encode the Eurocin sequence as identified above. The sequence of the PCR fragment is shown as SEQ ID NO:6.

The *Aspergillus* expression plasmid with the PCR product insert was named pMT2935 and is shown as SEQ ID NO:7.

Example 3

Expression of Eurocin in *Aspergillus* pMT2935 (see SEQ ID NO:7) was transformed into *Aspergillus oryzae* strain BECh2 (see international patent application WO 00/39322). 30 transformants were re-isolated twice under selective and non-inducing conditions on Cove minimal plates with sucrose and acetamide. To test expression of Eurocin, transformants were grown for 6 days at 30 degrees celcius in tubes with 10 ml YPM (2% peptone, 1% yeast extract, 2% maltose). Supernatants were run on NuPage 10% Bis-Tris SDS gels (Invitrogen) as recommended by the manufacturer with MES running buffer to allow separation in the low Mw range. The *Aspergillus oryzae* transformants grew well even when induced for the expression of Eurocin. A distinct band of the size expected for Eurocin was seen in most transformants whereas this band was not seen in the untransformed host strains *A. oryzae* BECh2.

Example 4

Purification of Eurocin

The fermentation broth was filtered through a 0.22 μm Corning 431118 filter and pH adjusted to 4.0 using formic acid. Filtering through a 0.22 μm filter was repeated to remove additional precipitate after adjusting pH. The conductivity was measured and adjusted to approximately 10 mS $cm^{-1}$ by adding MQ-water (Millipore). The filtrate was then loaded onto a 12 ml Source 30S (Amersham Biosciences 17-1273-01) column using an AKTA explorer HPLC instrument. Loading buffer was 50 mM formic acid, pH 4 (buffer A).

Eurocin was eluted using a gradient of 0-100% buffer B of 20 column volumes. Buffer B was 50 mM formic acid, 2 M sodium chloride, pH 4.0. The identity of the purified fractions was checked by MALDI-TOF MS (Voyager DE Pro instrument, Applied Biosystems) and the purity roughly checked by SDS-PAGE (Invitrogen, NuPage 12% Bis-Tris/MES, stained with Gel code Blue Stain Reagent, Pierce 24592)

Fractions containing the relevant compound (based on MALDI-TOF MS) were pooled and concentrated on an Amicon Ultra 5000 Da MWCO filter (Millipore UFC900524). Centrifugation was done at 4000 g for approximately 30 minutes. The solution was then desalted by washing three times with 0.01% acidic acid using the same filter and centrifugation conditions.

The product was analyzed for correct sequence and purity by amino acid analysis and MALDI-TOF MS. The measured mass of Eurocin was 4339 Da. The theoretical molecular weight is 4338.8 Da, average, based on amino acids 1 to 42 of SEQ ID NO:2.

The stock solution was stored at –20° C.

Example 5

Evaluation of Antimicrobial Activity

Purified Eurocin was evaluated for antimicrobial activity in a microdillution assay. The Minimal Inhibitory Concentration (MIC) was determined following the NCCLS/CLSI guidelines from CLSI (Clinical and Laboratory Standards Institute).

Eurocin was tested at the following concentrations: 32; 16; 8; 4; 2; 1; 0.50; 0.25; 0.13; and 0.06 μg/ml.

As shown in Table 2, Eurocin exhibits strong antimicrobial activity against a variety of ATCC strains.

TABLE 2

Antimicrobial activity of Eurocin

| Strain | MIC (μg/ml) |
| --- | --- |
| *Staphylococcus aureus*, ATCC 29213 | 16 |
| *Staphylococcus epidermidis*, ATCC 12228 | 16 |
| *Staphylococcus carnosus*, ATCC 51365 | 8 |
| *Streptococcus pneumoniae*, ATCC 49619 | 0.25 |
| *Streptococcus pyogenes*, ATCC 12344 | 0.13 |
| *Enterococcus faecium*, ATCC 49624 | 16 |
| *Micrococcus luteus*, ATCC 9341 | 0.5 |

Example 6

Using the HMM Files from the PFAM Database to Identify a Defensin

Sequence analysis using hidden markov model profiles (HMM profiles) may be carried out either online on the Internet or locally on a computer using the well-known HMMER freely available software package. The current version is HMMER 2.3.2 from October 2003.

The HMM profiles may be obtained from the well-known PFAM database. The current version is PFAM 16.0 from November 2004. Both HMMER and PFAM are available for all computer platforms from e.g. Washington University in St. Louis (USA), School of Medicine (http://pfam.wustl.edu and http://hmmer.wustl.edu).

If a query amino acid sequence, or a fragment thereof, belongs to one of the following five PFAM families, the amino acid sequence is a defensin according to the present invention:

Defensin_beta or "Beta Defensin", accession number: PF00711;

Defensin_propep or "Defensin propeptide", accession number: PF00879;

Defensin_1 or "Mammalian defensin", accession number: PF00323;

Defensin_2 or "Arthropod defensin", accession number: PF01097;

Gamma-thionin or "Gamma-thionins family", accession number: PF00304.

An amino acid sequence belongs to a PFAM family, according to the present invention, if it generates an E-value which is greater than 0.1, and a score which is larger or equal to zero, when the PFAM database is used online, or when the hmmpfam program (from the HMMER software package) is used locally.

When the sequence analysis is carried out locally using the hmmpfam program, it is necessary to obtain (download) the HMM profiles from the PFAM database. Two profiles exist for each family; xxx_ls.hmm for glocal searches, and xxx_fs.hmm for local searches ("xxx" is the name of the family). That makes a total of ten profiles for the five families mentioned above.

These ten profiles may be used individually, or joined (appended) into a single profile (using a text editor—the profiles are ASCII files) that could be named e.g. defensin.hmm. A query amino acid sequence can then be evaluated by using the following command line:

hmmpfam-E 0.1 defensin.hmm sequence_file wherein "sequence_file" is a file with the query amino acid sequence in any of the formats recognized by the HMMER software package.

If the score is larger or equal to zero (0.0), and the E-value is greater than 0.1, the query amino acid sequence is a defensin according to the present invention.

The PFAM database is further described in Bateman et al. (2004) "The Pfam Protein Families Database", Nucleic Acids Research, Vol. 32 (Database Issue) pp. D138-D141.

The invention claimed is:

1. A method for killing or inhibiting growth of microbial cells comprising contacting the microbial cells with an antimicrobial peptide, wherein the antimicrobial peptide is encoded by a polynucleotide which hybridizes under high stringency conditions with (i) nucleotides 145 to 270 of SEQ ID NO:1, (ii) the cDNA sequence contained in nucleotides 1 to 270 of SEQ ID NO:1, or (iii) the complementary strand of (i) or (ii), wherein the high stringency conditions are defined as prehybridization and hybridization at 42° C. in 5×SSPE, 0.3% SDS, 200 mg/ml sheared and denatured salmon sperm DNA, and 50% formamide, following standard Southern blotting procedures for 12 to 24 hours, followed by washing three times each for 15 minutes using 2×SSC, 0.2% SDS at 65° C.

2. The method of claim 1, wherein the antimicrobial peptide is encoded by a polynucleotide which hybridizes under very high stringency conditions with (i) nucleotides 145 to 270 of SEQ ID NO:1, (ii) the cDNA sequence contained in nucleotides 1 to 270 of SEQ ID NO:1, or (iii) the complementary strand of (i) or (ii), wherein the very high stringency conditions are defined as prehybridization and hybridization at 42° C. in 5×SSPE, 0.3% SDS, 200 µg/ml sheared and denatured salmon sperm DNA, and 50% formamide, following standard Southern blotting procedures for 12 to 24 hours, followed by washing three times each for 15 minutes using 2×SSC, 0.2% SDS at 70° C.

3. A method for killing or inhibiting growth of microbial cells comprising contacting the microbial cells with an antimicrobial peptide, wherein the antimicrobial peptide has at least 90% identity with amino acids 1 to 42 of SEQ ID NO:2.

4. The method of claim 3, wherein the antimicrobial peptide has at least 95% identity with amino acids 1 to 42 of SEQ ID NO:2.

5. The method of claim 3, wherein the antimicrobial peptide has at least 96% identity with amino acids 1 to 42 of SEQ ID NO:2.

6. The method of claim 3, wherein the antimicrobial peptide has at least 97% identity with amino acids 1 to 42 of SEQ ID NO:2.

7. The method of claim 3, wherein the antimicrobial peptide has at least 98% identity with amino acids 1 to 42 of SEQ ID NO:2.

8. The method of claim 3, wherein the antimicrobial peptide has at least 99% identity with amino acids 1 to 42 of SEQ ID NO:2.

9. The method of claim 3, wherein the antimicrobial peptide comprises amino acids 1 to 42 of SEQ ID NO:2.

10. The method of claim 3, wherein the antimicrobial peptide consists of amino acids 1 to 42 of SEQ ID NO:2.

* * * * *

SEQUENCE LISTING

<160> NUMBER OF SEQ ID NOS: 8

<210> SEQ ID NO 1
<211> LENGTH: 273
<212> TYPE: DNA
<213> ORGANISM: Eurotium amstelodami
<220> FEATURE:
<221> NAME/KEY: CDS
<222> LOCATION: (1)..(270)
<220> FEATURE:
<221> NAME/KEY: sig_peptide
<222> LOCATION: (1)..(60)
<220> FEATURE:
<221> NAME/KEY: mat_peptide
<222> LOCATION: (145)..(270)

<400> SEQUENCE: 1

```
atg cac ttc acc aag gtc tcc acc att ctt ttt acc atc ttc gcc gcc      48
Met His Phe Thr Lys Val Ser Thr Ile Leu Phe Thr Ile Phe Ala Ala
            -45                 -40                 -35 ggc atc atg gct gct ccc acc gaa gga gtc cgt gag gaa gcc gcc cct      96
Gly Ile Met Ala Ala Pro Thr Glu Gly Val Arg Glu Glu Ala Ala Pro
        -30                 -25                 -20 ggc cag gag gtt tac ccc gac gaa cct cct gct tct ctg acc aag cgt     144
Gly Gln Glu Val Tyr Pro Asp Glu Pro Pro Ala Ser Leu Thr Lys Arg
    -15                 -10                  -5                 -1 ggc ttc gga tgt cct ggt gat gcc tac cag tgc agt gaa cac tgc agg     192
Gly Phe Gly Cys Pro Gly Asp Ala Tyr Gln Cys Ser Glu His Cys Arg
  1               5                  10                 15 gcc ctg ggc ggt gga cgc act gga gga tac tgt gct gga cct tgg tat     240
Ala Leu Gly Gly Gly Arg Thr Gly Gly Tyr Cys Ala Gly Pro Trp Tyr
                20                  25                  30 ttg ggt cac cct acc tgc acc tgt tct ttc taa                         273
Leu Gly His Pro Thr Cys Thr Cys Ser Phe
        35                  40
```

<210> SEQ ID NO 2
<211> LENGTH: 90
<212> TYPE: PRT
<213> ORGANISM: Eurotium amstelodami

<400> SEQUENCE: 2

Met His Phe Thr Lys Val Ser Thr Ile Leu Phe Thr Ile Phe Ala Ala
            -45                 -40                 -35

Gly Ile Met Ala Ala Pro Thr Glu Gly Val Arg Glu Glu Ala Ala Pro
        -30                 -25                 -20

Gly Gln Glu Val Tyr Pro Asp Glu Pro Pro Ala Ser Leu Thr Lys Arg

```
                -15                 -10                  -5                  -1
Gly Phe Gly Cys Pro Gly Asp Ala Tyr Gln Cys Ser Glu His Cys Arg
  1               5                  10                  15

Ala Leu Gly Gly Gly Arg Thr Gly Tyr Cys Ala Gly Pro Trp Tyr
                 20                  25                  30

Leu Gly His Pro Thr Cys Thr Cys Ser Phe
             35                  40

<210> SEQ ID NO 3
<211> LENGTH: 90
<212> TYPE: PRT
<213> ORGANISM: Eurotium amstelodami
<220> FEATURE:
<221> NAME/KEY: SIGNAL
<222> LOCATION: (1)..(20)
<220> FEATURE:
<221> NAME/KEY: PROPEP
<222> LOCATION: (21)..(48)
<220> FEATURE:
<221> NAME/KEY: mat_peptide
<222> LOCATION: (49)..(90)

<400> SEQUENCE: 3

Met His Phe Thr Lys Val Ser Thr Ile Leu Phe Thr Ile Phe Ala Ala
                -45                 -40                 -35

Gly Ile Met Ala Ala Pro Thr Glu Gly Val Arg Glu Glu Ala Ala Pro
            -30                 -25                 -20

Gly Gln Glu Val Tyr Pro Asp Glu Pro Pro Ala Ser Leu Thr Lys Arg
        -15                 -10                  -5                  -1

Gly Phe Gly Cys Pro Gly Asp Ala Tyr Gln Cys Ser Glu His Cys Arg
  1               5                  10                  15

Ala Leu Gly Gly Gly Arg Thr Gly Tyr Cys Ala Gly Pro Trp Tyr
                 20                  25                  30

Leu Gly His Pro Thr Cys Thr Cys Ser Phe
             35                  40

<210> SEQ ID NO 4
<211> LENGTH: 34
<212> TYPE: DNA
<213> ORGANISM: Artificial
<220> FEATURE:
<223> OTHER INFORMATION: Primer A

<400> SEQUENCE: 4
tcttggatcc accatgcact tcaccaaggt ctcc                              34

<210> SEQ ID NO 5
<211> LENGTH: 34
<212> TYPE: DNA
<213> ORGANISM: Artificial
<220> FEATURE:
<223> OTHER INFORMATION: Primer B

<400> SEQUENCE: 5
tcttctcgag ttagaaagaa caggtgcagg tagg                              34

<210> SEQ ID NO 6
<211> LENGTH: 296
<212> TYPE: DNA
<213> ORGANISM: Eurotium amstelodami
<220> FEATURE:
<221> NAME/KEY: misc_feature
<222> LOCATION: (1)..(296)
<223> OTHER INFORMATION: PCR fragment
```

```
<400> SEQUENCE: 6
tcttggatcc accatgcact tcaccaaggt ctccaccatt cttttttacca tcttcgccgc      60 cggcatcatg gctgctccca ccgaaggagt ccgtgaggaa gccgcccctg ccaggaggt      120 ttaccccgac gaacctcctg cttctctgac caagcgtggc ttcggatgtc ctggtgatgc     180
ctaccagtgc agtgaacact gcagggccct gggcggtgga cgcactggag gatactgtgc     240
tggaccttgg tatttgggtc accctacctg cacctgttct ttctaactcg agaaga        296

<210> SEQ ID NO 7
<211> LENGTH: 7218
<212> TYPE: DNA
<213> ORGANISM: Plasmid pMT2935

<400> SEQUENCE: 7
tgtataagct agcttatggt gttttgatca ttttaaattt ttatatggcg ggtggtgggc      60
aactcgcttg cgcgggcaac tcgcttaccg attacgttag gctgatatt tacgtaaaaa     120 tcgtcaaggg atgcaagacc aaaccgttaa atttccggag tcaacagcat ccaagcccaa     180
gtccttcacg gagaaacccc agcgtccaca tcacgagcga aggaccacct ctaggcatcg     240
gacgcaccat ccaattagaa gcagcaaagc gaaacagccc aagaaaaagg tcggcccgtc     300
ggccttttct gcaacgctga tcacgggcag cgatccaacc aacaccctcc agagtgacta     360
ggggcggaaa tttatcggga ttaatttcca ctcaaccaca aatcacagtc gtccccggta     420
atttaacggc tgcagacggc aatttaacgg cttctgcgaa tcgcttggat tccccgcccc     480
tggccgtaga gcttaaagta tgtcccttgt cgatgcgatg tatgaattca tggtgttttg     540
atcattttaa atttttatat ggcgggtggt gggcaactcg cttgcgcggg caactcgctt     600
accgattacg ttagggctga tatttacgta aaaatcgtca agggatgcaa gaccaaaccg     660
ttaaatttcc ggagtcaaca gcatccaagc ccaagtcctt cacggagaaa ccccagcgtc     720
cacatcacga gcgaaggacc acctctaggc atcggacgca ccatccaatt agaagcagca     780
aagcgaaaca gcccaagaaa aaggtcggcc cgtcggcctt ttctgcaacg ctgatcacgg     840
gcagcgatcc aaccaacacc ctccagagtg actaggggcg gaaatttatc gggattaatt     900
tccactcaac cacaaatcac agtcgtcccc ggtaatttaa cggctgcaga cggcaattta     960
acggcttctg cgaatcgctt ggattccccg ccctggccg tagagcttaa agtatgtccc    1020
ttgtcgatgc gatgtatcac aacatataaa tactggcaag ggatgccatg cttggagttt    1080
ccaactcaat ttacctctat ccacacttct cttccttcct caatcctcta tatacacaac    1140
tggggatcca ccatgcactt caccaaggtc tccaccattc tttttaccat cttcgccgcc    1200
ggcatcatgg ctgctcccac cgaaggagtc cgtgaggaag ccgcccctgg ccaggaggtt    1260
taccccgacg aacctcctgc ttctctgacc aagcgtggct tcggatgtcc tggtgatgcc    1320
taccagtgca gtgaacactg cagggccctg gcggtggac gcactggagg atactgtgct    1380
ggaccttggt atttgggtca ccctacctgc acctgttctt tctaactcga gatctagagg    1440
gtgactgaca cctggcggta gacaatcaat ccatttcgct atagttaaag gatgggatg    1500 agggcaattg gttatatgat catgtatgta gtgggtgtgc ataatagtag tgaaatggaa    1560
gccaagtcat gtgattgtaa tcgaccgacg gaattgagga tatccggaaa tacagacacc    1620
gtgaaagcca tggtctttcc ttcgtgtaga agaccagaca gacagtccct gatttaccct    1680
tgcacaaagc actagaaaat tagcattcca tccttctctg cttgctctgc tgatatcact    1740
gtcattcaat gcatagccat gagctcatct tagatccaag cacgtaattc catagccgag    1800
```

```
gtccacagtg gagcagcaac attcccatc attgctttcc ccaggggcct cccaacgact   1860
aaatcaagag tatatctcta ccgtccaata gatcgtcttc gcttcaaaat ctttgacaat   1920
tccaagaggg tccccatcca tcaaacccag ttcaataata gccgagatgc atggtggagt   1980
caattaggca gtattgctgg aatgtcgggg ccagttggcc gggtggtcat tggccgcctg   2040
tgatgccatc tgccactaaa tccgatcatt gatccaccgc ccacgaggcg cgtctttgct   2100
ttttgcgcgg cgtccaggtt caactctctc ctctagactg gaaacgcaac cctgaaggga   2160
ttcttccttt gagagatgga agcgtgtcat atctcttcgg ttctacggca ggttttttc    2220 tgctctttcg tagcatggca tggtcacttc agcgcttatt tacagttgct ggtattgatt   2280
tcttgtgcaa attgctatct gacacttatt agctatggag tcaccacatt tcccagcaac   2340
ttccccactt cctctgcaat cgccaacgtc ctctcttcac tgagtctccg tccgataacc   2400
tgcactgcaa ccggtgcccc atggtacgcc tccggatcat actcttcctg cacgagggca   2460
tcaagctcac taaccgcctt gaaactctca ttcttcttat cgatgttctt atccgcaaag   2520
gtaaccggaa caaccacgct cgtgaaatcc agcaggttga tcacagaggc atacccatag   2580
taccggaact ggtcatgccg taccgcagcg gtaggcgtaa tcggcgcgat gatgcgtcc    2640 agttccttcc cggccttttc ttcagcctcc cgccatttct caaggtactc catctggtaa   2700
ttccacttct ggagatgcgt gtcccagagc tcgttcatgt taacagcttt gatgttcggg   2760
ttcagtaggt ctttgatatt tggaatcgcc ggctcgccgg atgcactgat atcgcgcatt   2820
acgtcggcgc tgccgtcagc cgcgtagata tgggagatga atcgtggcc gaaatcgtgc   2880 ttgtatggcg tccacggggt cacggtgtga ccggctttgg cgagtgcggc gacggtggtt   2940
tccacgccgc gcaggatagg agggtgtgga aggacattgc cgtcgaagtt gtagtagccg   3000
atattgagcc cgccgttctt gatcttggag gcaataatgt ccgactcgga ctggcgccag   3060
ggcatgggga tgaccttgga gtcgtatttc catggctcct gaccgaggac ggatttggtg   3120
aagaggcgga ggtctaacat acttcatcag tgactgccgg tctcgtatat agtataaaaa   3180
gcaagaaagg aggacagtgg aggcctggta tagagcagga aaagaaggaa gaggcgaagg   3240
actcaccctc aacagagtgc gtaatcggcc cgacaacgct gtgcaccgtc tcctgaccct   3300
ccatgctgtt cgccatcttt gcatacggca gccgcccatg actcggcctt agaccgtaca   3360
ggaagttgaa cgcggccggc actcgaatcg agccaccgat atccgttcct acaccgatga   3420
cgccaccacg aatcccaacg atcgcaccct caccaccaga actgccgccg cacgaccagt   3480
tcttgttgcg tgggttgacg gtgcgcccga tgatgttgtt gactgtctcg cagaccatca   3540
gggtctgcgg gacagaggtc ttgacgtaga agacggcacc ggctttgcgg agcatggttg   3600
tcagaaccga gtcccttcg tcgtacttgt ttagccatga gatgtagccc attgatgttt    3660
cgtagccctg gtggcatatg ttagctgaca aaaagggaca tctaacgact taggggcaac   3720
ggtgtacctt gactcgaagc tggtctttga gagagatggg gaggccatgg agtggaccaa   3780
cgggtctctt gtgctttgcg tagtattcat cgagttccct tgcctgcgcg agagcggcgt   3840
cagggaagaa ctcgtgggcg cagtttgtct gcacagaagc cagcgtcagc ttgatagtcc   3900
cataaggtgg cgttgttaca tctccctgag aggtagaggg gaccctacta actgctgggc   3960
gattgctgcc cgtttacaga atgctagcgt aacttccacc gaggtcaact ctccggccgc   4020
cagcttggac acaagatctg cagcggaggc ctctgtgatc ttcagttcgg cctctgaaag   4080
gatcaccgat ttctttggga aatcaataac gctgtcttcc gcaggcagcg tctggacttt   4140
ccattcatca gggatggttt ttgcgaggcg ggcgcgctta tcagcggcca gttcttccca   4200
```

```
ggattgaggc attctgtgtt agcttatagt caggatgttg gctcgacgag tgtaaactgg    4260
gagttggcat gagggttatg taggcttctt tagccccgca tcccctcat tctcctcatt    4320
gatcccgggg gagcggatgg tgttgataag agactaatta tagggtttag ctggtgccta    4380
gctggtgatt ggctggcttc gccgaatttt acgggccaag aaagctgca gaaccgcggc    4440
actggtaaac ggtaattaag ctatcagccc catgctaacg agtttaaatt acgtgtattg    4500
ctgataaaca ccaacagagc tttactgaaa gatgggagtc acggtgtggc ttccccactg    4560
cgattattgc acaagcagcg agggcgaact tgactgtcgt cgctgagcag cctgcagtca    4620
aacatacata tatatcaacc gcgaagacgt ctggccttgt agaacacgac gctccctagc    4680
aacacctgcc gtgtcagcct ctacggttgt tacttgcatt caggatgctc tccagcgggc    4740
gagctattca aaatattcaa agcaggtatc tcgtattgcc aggattcagc tgaagcaaca    4800
ggtgccaagg aaatctgcgt cggttctcat ctgggcttgc tcggtcctgg cgtagatcta    4860
gagtcgacct gcaggcatgc ggcgtaatca tggtcatagc tgtttcctgt gtgaaattgt    4920
tatccgctca caattccaca caacatacga gccggaagca taaagtgtaa agcctggggt    4980
gcctaatgag tgagctaact cacattaatt gcgttgcgct cactgcccgc tttccagtcg    5040
ggaaacctgt cgtgccagct gcattaatga atcggccaac gcgcggggag aggcggtttg    5100
cgtattgggc gctcttccgc ttcctcgctc actgactcgc tgcgctcggt cgttcggctg    5160
cggcgagcgg tatcagctca ctcaaaggcg gtaatacggt tatccacaga atcaggggat    5220
aacgcaggaa agaacatgtg agcaaaaggc cagcaaaagg ccaggaaccg taaaaaggcc    5280
gcgttgctgg cgtttttcca taggctccgc cccctgacg agcatcacaa aaatcgacgc    5340
tcaagtcaga ggtggcgaaa cccgacagga ctataaagat accaggcgtt tccccctgga    5400
agctccctcg tgcgctctcc tgttccgacc ctgccgctta ccggatacct gtccgccttt    5460
ctcccttcgg gaagcgtggc gctttctcat agctcacgct gtaggtatct cagttcggtg    5520
taggtcgttc gctccaagct gggctgtgtg cacgaacccc ccgttcagcc cgaccgctgc    5580
gccttatccg gtaactatcg tcttgagtcc aacccggtaa gacacgactt atcgccactg    5640
gcagcagcca ctggtaacag gattagcaga gcgaggtatg taggcggtgc tacagagttc    5700
ttgaagtggt ggcctaacta cggctacact agaagaacag tatttggtat ctgcgctctg    5760
ctgaagccag ttaccttcgg aaaaagagtt ggtagctctt gatccgacaa acaaaccacc    5820
gctggtagcg gtggtttttt tgtttgcaag cagcagatta cgcgcagaaa aaaggatct    5880
caagaagatc ctttgatctt ttctacgggg tctgacgctc agtggaacga aaactcacgt    5940
taagggattt tggtcatgag attatcaaaa aggatcttca cctagatcct tttaaattaa    6000
aaatgaagtt ttaaatcaat ctaaagtata tatgagtaaa cttggtctga cagttaagca    6060
aggattttct taacttcttc ggcgacagca tcaccgactt cggtggtact gttggaacca    6120
cctaaatcac cagttctgat acctgcatcc aaaacctttt taactgcatc ttcaatggcc    6180
ttaccttctt caggcaagtt caatgacaat ttcaacatca ttgcagcaga caagatagtg    6240
gcgataggggt tgaccttatt ctttggcaaa tctggagcag aaccgtggca tggttcgtac    6300
aaaccaaatg cggtgttctt gtctggcaaa gaggccaagg acgcagatgg caacaaaccc    6360
aaggaacctg ggataacgga ggcttcatcg gagatgatat caccaaacat gttgctggtg    6420
attataatac catttaggtg ggttgggttc ttaactagga tcatggcggc agaatcaatc    6480
aattgatgtt gaaccttcaa tgtagggaat tcgttcttga tggtttcctc cacagttttt    6540
ctccataatc ttgaagaggc caaaacatta gctttatcca aggaccaaat aggcaatggt    6600
```

```
ggctcatgtt gtagggccat gaaagcggcc attcttgtga ttctttgcac ttctggaacg    6660
gtgtattgtt cactatccca agcgacacca tcaccatcgt cttcctttct cttaccaaag    6720
taaatacctc ccactaattc tctgacaaca acgaagtcag tacctttagc aaattgtggc    6780
ttgattggag ataagtctaa aagagagtcg gatgcaaagt tacatggtct taagttggcg    6840
tacaattgaa gttctttacg gattttagt aaaccttgtt caggtctaac actgccggta    6900
ccccatttag gaccacccac agcacctaac aaaacggcat cagccttctt ggaggcttcc    6960
agcgcctcat ctggaagtgg aacacctgta gcatcgatag cagcaccacc aattaaatga    7020
ttttcgaaat cgaacttgac attggaacga acatcagaaa tagctttaag aaccttaatg    7080
gcttcggctg tgatttcttg accaacgtgg tcacctggca aaacgacgat cttcttaggg    7140
gcagacatac tcttcctttt tcaatattat tgaagcattt atcagggtta ttgtctcatg    7200
agcggataca tatttgaa                                                  7218

<210> SEQ ID NO 8
<211> LENGTH: 2403
<212> TYPE: DNA
<213> ORGANISM: Plasmid pMhas5

<400> SEQUENCE: 8
cgataagcta gcttcacgct gccgcaagca ctcagggcgc aagggctgct aaaggaagcg      60
gaacacgtag aaagccagtc cgcagaaacg gtgctgaccc cggatgaatg tcagctactg     120
ggctatctgg acaagggaaa acgcaagcgc aaagagaaag caggtagctt gcagtgggct     180
tacatggcga tagctagact gggcggtttt atggacagca agcgaaccgg aattgccagc     240
tggggcgccc tctggtaagg ttgggaagcc ctgcaaagta aactggatgg ctttcttgcc     300
gccaaggatc tgatggcgca ggggatcaag atctgatcaa gagacaggat gaggatcgtt     360
tcgcatgatt gaacaagatg gattgcacgc aggttctccg gccgcttggg tggagaggct     420
attcggctat gactgggcac aacagacaat cggctgctct gatgccgccg tgttccggct     480
gtcagcgcag gggcgcccgg ttcttttttgt caagaccgac ctgtccggtg ccctgaatga     540
actccaagac gaggcagcgc ggctatcgtg gctggccacg acgggcgttc cttgcgcagc     600
tgtgctcgac gttgtcactg aagcgggaag ggactggctg ctattgggcg aagtgccggg     660
gcaggatctc ctgtcatctc accttgctcc tgccgagaaa gtatccatca tggctgatgc     720
aatgcggcgg ctgcatacgc ttgatccggc tacctgccca ttcgaccacc aagcgaaaca     780
tcgcatcgag cgagcacgta tcggatgga agccggtctt gtcgatcagg atgatctgga     840
cgaagagcat caggggctcg cgccagccga actgttcgcc aggctcaagg cgcggatgcc     900
cgacggcgag gatctcgtcg tgacccatgg cgatgcctgc ttgccgaata tcatggtgga     960
aaatggccgc ttttctggat tcatcgactg tggccggctg ggtgtggcgg accgctatca    1020
ggacatagcg ttggctaccc gtgatattgc tgaagagctt ggcggcgaat gggctgaccg    1080
cttcctcgtg ctttacggta tcgccgctcc cgattcgcag cgcatcgcct tctatcgcct    1140
tcttgacgag ttcttctgag cgggactctg gggttcgcga tgataagctg tcaaacatga    1200
gaattacaac ttatatcgta tggggctgac ttcaggtgct acatttgaag agataaattg    1260
cactgaaatc tagaaatatt ttatctgatt aataagatga tcttcttgag atcgttttgg    1320
tctgcgcgta atctcttgct ctgaaaacga aaaaccgcc ttgcagggcg ttttttcgaa    1380
ggttctctga gctaccaact cttttgaaccg aggtaactgg cttggaggag cgcagtcacc    1440
aaaacttgtc ctttcagttt agccttaacc ggcgcatgac ttcaagacta actcctctaa    1500
```

-continued

```
atcaattacc agtggctgct gccagtggtg cttttgcatg tctttccggg ttggactcaa    1560
gacgatagtt accggataag gcgcagcggt cggactgaac gggggggttcg tgcatacagt    1620 ccagcttgga gcgaactgcc tacccggaac tgagtgtcag gcgtggaatg agacaaacgc    1680
ggccataaca gcggaatgac accggtaaac cgaaaggcag gaacaggaga gcgcacgagg    1740
gagccgccag gggaaacgcc tggtatcttt atagtcctgt cgggtttcgc caccactgat    1800
ttgagcgtca gatttcgtga tgcttgtcag ggggcggag cctatggaaa aacggctttg    1860
ccttctttcc tgcgttatcc cctgattctg tggataaccg tattaccgcc tttgagtgag    1920
ctgataccgc tcgccgcagc cgaacgaccg agcgcagcga gtcagtgagc gaggaagcgg    1980
aagagcgccc aatacgcaaa ccgcctctcc ccgcgcgttg gccgattcat taatgcagct    2040
ggcacgacag gtttcccgac tggaaagcgg gcagtgagcg caacgcaatt aatgtgagtt    2100
agctcactca ttaggcaccc caggctttac actttatgct tccggctcgt atgttgtgtg    2160
gaattgtgag cggataacaa tttcacacag gaattcacag ctatgctaga gcggccgctc    2220
gacctgcagg catgcaagct tggcactggc cgtcgtttta caacgtcgtg actgggaaaa    2280
ccctggcgtt acccaactta atcgccttgc agcacatccc cctttcgcca gctggcgtaa    2340
tagcgaagag gcccgcaccg atcgcccttc ccaacagttg cgcagcctga atggcgaatg    2400
gcg                                                                  2403
```